(12) United States Patent
Howell et al.

(10) Patent No.: US 8,029,555 B2
(45) Date of Patent: Oct. 4, 2011

(54) STENT INTRODUCER SYSTEM

(75) Inventors: Douglas D. Howell, Cape Elizabeth, ME (US); William S. Gibbons, Winston-Salem, NC (US); Matthew P. Carter, Dobson, NC (US); Victor D. Clark, Jr., Pfafftown, NC (US)

(73) Assignee: Cook Medical Technologies LLC, Bloomington, IN (US)

( * ) Notice: Subject to any disclaimer, the term of this patent is extended or adjusted under 35 U.S.C. 154(b) by 0 days.

(21) Appl. No.: 12/689,804

(22) Filed: Jan. 19, 2010

(65) Prior Publication Data
US 2010/0121426 A1    May 13, 2010

Related U.S. Application Data

(62) Division of application No. 11/095,208, filed on Mar. 31, 2005, now abandoned.

(60) Provisional application No. 60/558,721, filed on Mar. 31, 2004.

(51) Int. Cl.
*A61F 2/06* (2006.01)
(52) U.S. Cl. .................................................. 623/1.11
(58) Field of Classification Search ......... 623/1.11–1.12
See application file for complete search history.

(56) References Cited

U.S. PATENT DOCUMENTS

| | | | |
|---|---|---|---|
| 3,485,234 A | 12/1969 | Stevens | |
| 3,585,707 A | 6/1971 | Stevens | |
| 3,612,058 A | 10/1971 | Ackerman | |
| 3,657,744 A | 4/1972 | Ersek | |
| 4,056,854 A | 11/1977 | Boretos et al. | |
| 4,140,126 A | 2/1979 | Choudhury | |
| 4,306,562 A | 12/1981 | Osborne | |
| 4,503,569 A | 3/1985 | Dotter | |
| 4,516,972 A | 5/1985 | Samson | |
| 4,562,596 A | 1/1986 | Kornberg | |
| 4,580,568 A | 4/1986 | Gianturco | |
| 4,581,025 A | 4/1986 | Timmermans | |
| 4,655,771 A | 4/1987 | Wallsten | |
| 4,665,771 A | 5/1987 | Mitchell | |
| 4,665,905 A | 5/1987 | Brown | |
| 4,665,918 A | 5/1987 | Garza | |
| 4,676,229 A | 6/1987 | Krasnicki | |
| 4,705,511 A | 11/1987 | Kocak | |

(Continued)

FOREIGN PATENT DOCUMENTS

EP    0177330 B1 *   4/1986

(Continued)

OTHER PUBLICATIONS

Wilson et al., *A Self-Expanding Bifurcated Endovascular Graft for Abdominal Aortic Aneurysm Repair*, An Initial Study in a Canine Model, vol. 42, Sep. 1996, pp. M386-M393.

(Continued)

*Primary Examiner* — Gary Jackson
*Assistant Examiner* — Eric Blatt
(74) *Attorney, Agent, or Firm* — Brinks Hofer Gilson & Lione

(57) ABSTRACT

A stent delivery system for positioning a first and second stent the first and second branch lumens of a bifurcation. The stent delivery system includes stent introducers and a sheath or catheter having a frangible wall. A method of delivering stents to anatomies such as bifurcated ducts or vessels.

16 Claims, 11 Drawing Sheets

U.S. PATENT DOCUMENTS

| | | | |
|---|---|---|---|
| 4,732,152 A | 3/1988 | Wallsten | |
| 4,733,665 A | 3/1988 | Palmaz | |
| 4,768,507 A | 9/1988 | Fischell | |
| 4,793,348 A | 12/1988 | Palmaz | |
| 4,817,613 A | 4/1989 | Jaraczewski | |
| 4,830,003 A | 5/1989 | Wolff et al. | |
| 4,842,590 A | 6/1989 | Tanabe | |
| 4,875,468 A | 10/1989 | Krauter | |
| 4,875,480 A | 10/1989 | Imbert | |
| 4,898,591 A | 2/1990 | Jang | |
| 4,925,445 A | 5/1990 | Sakamoto | |
| 4,954,126 A | 5/1990 | Wallsten | |
| 4,950,227 A | 8/1990 | Savin | |
| 4,954,126 A | 9/1990 | Wallsten | |
| 4,969,891 A | 11/1990 | Gewertz | |
| 4,990,151 A | 2/1991 | Wallsten | |
| 4,994,066 A | 2/1991 | Voss | |
| 4,998,539 A | 3/1991 | Delsanti | |
| 5,019,057 A | 5/1991 | Truckal | |
| 5,019,090 A | 5/1991 | Pinchuk | |
| 5,026,377 A | 6/1991 | Burton | |
| 5,037,427 A | 8/1991 | Harada | |
| 5,045,072 A | 9/1991 | Castillo | |
| 5,057,092 A | 10/1991 | Webster | |
| 5,064,435 A | 11/1991 | Porter | |
| 5,069,674 A | 12/1991 | Fearnot | |
| 5,089,005 A | 2/1992 | Harada | |
| 5,104,388 A | 4/1992 | Quackenbush | |
| 5,104,399 A | 4/1992 | Lazarus | |
| 5,151,105 A | 9/1992 | Kwan-Gett | |
| 5,160,341 A | 11/1992 | Brenneman | |
| 5,190,520 A | 3/1993 | Fenton | |
| 5,197,978 A | 3/1993 | Hess | |
| 5,201,757 A | 4/1993 | Heyn | |
| 5,201,901 A | 4/1993 | Harada | |
| 5,217,440 A | 6/1993 | Frassica | |
| 5,221,270 A | 6/1993 | Parker | |
| 5,221,372 A | 6/1993 | Olson | |
| 5,222,971 A | 6/1993 | Willard et al. | |
| 5,250,071 A | 10/1993 | Palermo | |
| 5,254,107 A | 10/1993 | Soltesz | |
| 5,275,622 A | 1/1994 | Lazarus et al. | |
| 5,279,596 A | 1/1994 | Casteneda | |
| 5,290,295 A | 3/1994 | Querals | |
| 5,290,310 A | 3/1994 | Makower et al. | |
| 5,306,252 A | 4/1994 | Yutori | |
| 5,318,542 A | 6/1994 | Hirsch et al. | |
| 5,318,586 A | 6/1994 | Ereren | |
| 5,330,500 A | 7/1994 | Song | |
| 5,354,308 A | 10/1994 | Simon et al. | |
| 5,366,442 A | 11/1994 | Wang | |
| 5,375,612 A | 12/1994 | Cottenceau | |
| 5,387,235 A | 2/1995 | Chuter | |
| 5,391,172 A | 2/1995 | Williams et al. | |
| 5,415,664 A | 5/1995 | Pinchuk | |
| 5,417,708 A | 5/1995 | Hall et al. | |
| 5,425,756 A | 6/1995 | Heil et al. | |
| 5,449,373 A | 9/1995 | Pinchasik | |
| 5,456,695 A | 10/1995 | Dallemagne | |
| 5,464,449 A | 11/1995 | Ryan et al. | |
| 5,474,563 A | 12/1995 | Myler et al. | |
| 5,480,423 A | 1/1996 | Ravenscroft | |
| 5,484,444 A | 1/1996 | Braunschweiler et al. | |
| 5,489,295 A | 2/1996 | Piplani et al. | |
| 5,498,240 A | 3/1996 | Bagaoisan et al. | |
| 5,197,978 A | 5/1996 | Hess | |
| 5,514,154 A | 5/1996 | Lau | |
| 5,534,007 A | 7/1996 | St. Germain et al. | |
| 5,538,510 A | 7/1996 | Fontrirroche | |
| 4,655,771 A | 9/1996 | Wallsten | |
| 5,554,139 A | 9/1996 | Okajima | |
| 5,562,641 A | 10/1996 | Floimenblit | |
| 5,562,698 A | 10/1996 | Parker | |
| 5,562,726 A | 10/1996 | Chuter | |
| 5,569,295 A | 10/1996 | Lam | |
| 5,571,135 A | 11/1996 | Fraser et al. | |
| 5,571,168 A | 11/1996 | Toro | |
| 5,571,170 A | 11/1996 | Palmaz | |
| 5,591,197 A | 1/1997 | Orth | |
| 5,601,600 A | 2/1997 | Ton | |
| 5,603,698 A | 2/1997 | Roberts | |
| 5,603,721 A | 2/1997 | Lau | |
| 5,605,530 A | 2/1997 | Fischell | |
| 5,620,649 A | 4/1997 | Trotta | |
| 5,628,788 A | 5/1997 | Pinchuk | |
| 5,639,278 A | 6/1997 | Dereume et al. | |
| 5,647,857 A | 7/1997 | Anderson et al. | |
| 5,649,952 A | 7/1997 | Lam | |
| 5,653,743 A | 8/1997 | Martin | |
| 5,665,103 A | 9/1997 | Lafontaine et al. | |
| 5,669,924 A | 9/1997 | Shaknovich | |
| 5,674,208 A | 10/1997 | Berg | |
| 5,690,644 A | 11/1997 | Yurek | |
| 5,695,499 A | 12/1997 | Helgerson | |
| 5,697,971 A | 12/1997 | Fischell | |
| 5,700,269 A | 12/1997 | Pinchuk | |
| 5,702,418 A | 12/1997 | Ravenscroft | |
| 5,702,419 A | 12/1997 | Berry et al. | |
| 5,704,926 A | 1/1998 | Sutton | |
| 5,707,376 A | 1/1998 | Kavteladze | |
| 5,709,703 A | 1/1998 | Lukic et al. | |
| 5,720,735 A | 2/1998 | Dorros | |
| 5,728,158 A | 3/1998 | Lau | |
| 5,733,325 A | 3/1998 | Robinson et al. | |
| 5,735,859 A | 4/1998 | Fischell | |
| 5,735,893 A | 4/1998 | Lau | |
| 5,755,781 A | 5/1998 | Jayaraman | |
| 5,772,669 A | 6/1998 | Vrba | |
| 5,776,140 A | 7/1998 | Cottone | |
| 5,800,517 A | 9/1998 | Anderson et al. | |
| 5,833,694 A | 11/1998 | Poncet | |
| 5,843,090 A | 12/1998 | Schuetz | |
| 5,976,153 A | 11/1999 | Fischell et al. | |
| 5,984,964 A | 11/1999 | Roberts | |
| 6,019,778 A | 2/2000 | Wilson et al. | |
| 6,099,497 A | 8/2000 | Adams et al. | |
| 6,142,973 A | 11/2000 | Carleton et al. | |
| 6,159,238 A | 12/2000 | Killion et al. | |
| 6,228,110 B1 | 5/2001 | Munsinger | |
| 6,287,329 B1 | 9/2001 | Duerig et al. | |
| 4,733,665 C2 | 1/2002 | Palmaz | |
| 6,346,118 B1 | 2/2002 | Baker et al. | |
| 6,379,365 B1 | 4/2002 | Diaz | |
| 6,391,051 B2 | 5/2002 | Sullivan et al. | |
| 6,395,017 B1 | 5/2002 | Dwyer et al. | |
| 6,425,898 B1 | 7/2002 | Wilson et al. | |
| 6,454,744 B1 | 9/2002 | Spohn et al. | |
| 6,544,278 B1 | 4/2003 | Vrba et al. | |
| 6,562,049 B1 | 5/2003 | Norlander et al. | |
| 6,579,312 B2 | 6/2003 | Wilson | |
| 6,592,549 B2 | 7/2003 | Gerdts et al. | |
| 6,596,020 B2 | 7/2003 | Vardi | |
| 6,663,595 B2 | 12/2003 | Spohn et al. | |
| 7,022,131 B1 | 4/2006 | Derowe et al. | |
| 7,172,617 B2 | 2/2007 | Colgan et al. | |
| 7,476,243 B2 | 1/2009 | Eidenschink | |
| 7,641,684 B2 | 1/2010 | Hilaire | |
| 2001/0003161 A1 * | 6/2001 | Vardi et al. | |
| 2001/0034548 A1 * | 10/2001 | Vrba et al. | |
| 2001/0034549 A1 * | 10/2001 | Bartholf et al. | |
| 2002/0035391 A1 * | 3/2002 | Mikus et al. | |
| 2002/0161341 A1 * | 10/2002 | Stinson et al. | |
| 2003/0040789 A1 * | 2/2003 | Colgan et al. | |
| 2003/0139796 A1 * | 7/2003 | Sequin et al. | |
| 2003/0149444 A1 * | 8/2003 | Khaw | |
| 2003/0233115 A1 * | 12/2003 | Eversull et al. | |
| 2005/0085845 A1 * | 4/2005 | Hilaire et al. | |
| 2005/0125050 A1 * | 6/2005 | Carter et al. | |
| 2005/0192656 A1 * | 9/2005 | Eidenschink | |
| 2006/0100694 A1 * | 5/2006 | Globerman | |

FOREIGN PATENT DOCUMENTS

| | | | |
|---|---|---|---|
| EP | 0657147 A2 * | 6/1995 | |
| EP | 0657147 A3 * | 6/1995 | |
| EP | 0657147 B1 * | 6/1995 | |
| EP | 0696447 A2 * | 2/1996 | |
| EP | 0701800 A1 * | 3/1996 | |

| | | | |
|---|---|---|---|
| EP | 0701800 | B1 * | 3/1996 |
| EP | 0941716 | A2 * | 9/1999 |
| JP | 7-275369 | A | 10/1995 |
| WO | WO 95/34255 | * | 12/1995 |
| WO | WO 96/32078 | * | 10/1996 |
| WO | WO 96/35470 | * | 11/1996 |
| WO | WO 97/17911 | * | 5/1997 |
| WO | WO 97/17912 | * | 5/1997 |
| WO | WO 97/17913 | | 5/1997 |
| WO | WO 97/26936 | | 7/1997 |
| WO | WO 97/32623 | * | 9/1997 |
| WO | WO 98/10713 | * | 3/1998 |
| WO | WO 98/14224 | * | 4/1998 |
| WO | WO 98/20812 | A1 | 5/1998 |
| WO | WO 99/53865 | A1 | 10/1999 |
| WO | WO 00/41525 | A2 | 7/2000 |
| WO | WO 02/30329 | A2 | 4/2002 |
| WO | WO 2005/055882 | A1 | 6/2005 |

OTHER PUBLICATIONS

Castellani et al., *Resection and Reconstruction of the Carotid Bifurcation with Polytetrafluoroethylene Grafts; Operative Technique*, J. Cardiovasc Surg. vol. 32, 1991, pp. 426-435.

Cave-Bigley et al., *Use of a Ringed Intraluminal Graft in the Operative Management of Abdominal Aortic Aneurysms*, J. Surg. vol, 72, Issue 10, Oct. 1985, pp. 825-827.

Corson et al., *Large Diameter Expanded Polytetrafluoroethyulene Grafts for Infrarenal Aortic Aneurysm Surgery*, J. Cardiovasc Surg., vol. 31, issue 6, 1990, pp. 702-705.

Chuter et al., *Infrarenal Aortic Aneurysm Structure: Implications for Transfermoral Repair*, J. Vasc Surg. vol. 20, issue 1, Jul. 1994, pp. 44-50.

Van Son et al., *Bifurcated ("Y") Internal Thoracic Coronary Artery Grafts*, J. Thorac Cardiovas Surg. vol. 106, issue 5, Nov. 1993, pp. 945-946.

Cintora et al., *A clinical Survey of Aortobifemoral Bypass Using Two Inherently Different Graft Types*, Ann Surg. vol. 208, issue 5, Nov. 1998, pp. 625-630.

Calcagno et al., *Late Iliac Artery Aneurysms and Occlusive Disease After Aortic Tube Grafts for Abdoninal Aortic Aneurysm Repair*, Ann Surg. vol. 214, issue 6, Dec. 1991, pp. 733-736.

Chuter et al., *Transfermoral Insertion of a Bifurcated Endovascular Graft for Aortic Aneurysm Repair: The First 22 Patients*, J. Cardiovasc Surg. vol. 3, issue 2, Apr. 1995, pp. 121-128.

Moore, *The Role of Endovascular Grafting Technique in the Treatment of Infrarenal Abdominal Aortic Aneurysm*, J. Cardiovas Surg. vol. 3, issue 2, Apr. 1995, pp. 109-114.

Chuter et al., *Bifurcated Stent-Grafts for Endovascular Repair of Abdominal Aortic Aneurysm*, J. Surg. Endosc. vol. 8, issue 7, Jul. 1994, pp. 800-802.

Manresa et al., *Bifurcated Grafts in the Aorto-Femoral Tract*, J. Cardiovasc Surg., 1973 pp. 509-514.

Yusef et al., *Transfermoral Endoluminal Repair of Abdominal Aortic Aneurysm with Bifurcated Graft*, Lancet vol. 344, issue 8923, Sep. 3, 1994, pp. 650-651.

Green et al., *Evolution of Technologies in Endovascular Grafting*, J. Cardiovasc Surg. vol. 3, issue 2, Apr. 1994, pp. 101-107.

Rollins et al. *Self Expanding Metallic Stents: Preliminary Evaluation*, Radiology, Jun. 1987, pp. 739-742.

Mirich et al., *Percutaneously Placed Endovascular Grafts for Aortic Aneurysm*, Radiology, Mar. 1989, pp. 1033-1037.

Lawrence Jr., et al., *Percutaneous Endovascular Graft: Experimental Evaluation*, Radiology, May 1987, pp. 357-360.

Dobben et al., *Prostatic Urethra Dilation with the Gianturco Self-Expanding Metallic Stent*, AJR, Apr. 1991, pp. 757-761.

Irie et al., *Relocatable Gianturco Expandable Metallic Stents*, Radiology vol. 178, No. 2, pp. 575-578.

Olearchuk et al., *Bifurcated ("Y") Internal Thoracic Coronary Artery Grafts*, J. Thorac Cardiovasc Surg. vol. 103, issue 3, Mar. 1992, p. 601.

Yoshioka et al., *Self-Expanding Endovascular Graft: An Experimental Study in Dogs*, AJR 151, Oct. 1988, pp. 673-676.

Cook Vascular Incorporated; Introducer Sets: Peel-Away™ Introducer Sets; product description obtained at the internet address: http://www.cookvascular.com/introducers. shtml; date unknown; two pages.

International Search Report from corresponding International Application No. PCT/US2005/010904, mailing date Aug. 8, 2005; 12 pages.

Interview Summary mailed Jan. 26, 2010 for U.S. Appl. No. 10/728,589.

Advisory Action mailed Nov. 2, 2009 for U.S. Appl. No. 10/728,589.
Office Action mailed Aug. 13, 2009 for U.S. Appl. No. 10/728,589.
Office Action mailed Feb. 3, 2009 for U.S. Appl. No. 10/728,589.
Advisory Action mailed Jul. 29, 2008 for U.S. Appl. No. 10/728,589.
Office Action mailed May 13, 2008 for U.S. Appl. No. 10/728,589.
Office Action mailed Nov. 21, 2007 for U.S. Appl. No. 10/728,589.
Advisory Action mailed Aug. 6, 2007 for U.S. Appl. No. 10/728,589.
Office Action mailed May 30, 2007 for U.S. Appl. No. 10/728,589.
Office Action mailed Dec. 7, 2006 for U.S. Appl. No. 10/728,589.
Office Action mailed Oct. 17, 2006 for U.S. Appl. No. 10/728,589.

* cited by examiner

STENT INTRODUCER SYSTEM

RELATED APPLICATIONS

This application is a divisional application of U.S. application Ser. No. 11/095,208, filed Mar. 31, 2005, which claims the benefit of U.S. Provisional Application Ser. No. 60/558,721, filed Mar. 31, 2004, entitled "Stent Introducer System." These applications are incorporated by reference herein in their entirety.

TECHNICAL FIELD

This invention generally relates to medical devices, and more particularly to devices for delivering stents to a target anatomy.

BACKGROUND

Stents are elongate tubes that are used to prop open occluded or narrowed vessels or body lumens. Among other things, stents are often used to maintain the patency of the biliary tree, or common bile duct. FIG. 1 is a partial, cross-sectional view of a biliary system 2 showing the common bile duct 2a, the left hepatic duct 2b, the right hepatic duct 2c, the gall bladder 2d, the pancreas 2e and the duodenum 2f.

Strictures or occlusions that develop in the upper common bile duct and/or the left and right hepatic ducts can interfere with the proper drainage of those ducts. FIG. 2 illustrates a partial cross-sectional view of the biliary system 2 having strictures 3 within the common bile duct 2a, the left hepatic duct 2b and the right hepatic duct 2c. One method of establishing proper drainage through the diseased ducts is to prop open the ducts by placing stents, such as self-expanding biliary stents, within the diseased ducts. Because of the branched configuration of the duct anatomy it is often necessary to place two or more stents in an overlying or side-by-side configuration.

However, currently available stent and introducer geometries are such that placement of a first stent often impedes placement of a second stent. FIG. 3 illustrates the problems associated with the prior art method of placing stents in the common bile duct 2a and the left and right hepatic ducts 2b, 2c. That is, placing stent 16 within the common bile duct 2a and the left hepatic duct 2b impedes subsequent access to the stricture in the right hepatic duct 2c. This prevents placement of a stent in the right hepatic duct 2c.

FIG. 3A illustrates one problem encountered in the prior art by placing two stents sequentially. That is, once the first stent is deployed, it impedes insertion of the second introducer 20 used to deploy the second stent. An alternative to sequential deployment of the stents is simultaneous deployment. Simultaneous deployment, however, requires the side-by-side arrangement of two stent introducers within the working channel of an endoscope. Depending on the size of the stents to be placed and the limited size of the working channel of the endoscope, this option may be unworkable.

Consequently, there is a need for a self-expanding stent delivery system which overcomes the problems associated with prior art delivery systems. Specifically, there is a need for a self-expanding stent delivery system which allows the physician to sequentially place a first and second stent in the side branches and main lumen of a bifurcation.

SUMMARY OF THE INVENTION

Accordingly, it is an object of the present invention to provide a medical device, method, and kit having features that resolve or improve on one or more of the above-described drawbacks.

The foregoing object is obtained by providing a stent delivery system having a first introducer used to deploy a first stent, and a sheath or catheter used to receive a second introducer, which in turn is used to deploy a second stent. The first introducer and the catheter can be simultaneously deployed, for example, in a staggered configuration, through the working channel of an endoscope. Once the first stent is deployed, the catheter facilitates delivery of the second introducer to the target anatomy. The catheter or sheath can be splittable.

In another aspect, wire guides are used to guide the placement of the first introducer, the catheter, and the second introducer.

In yet another aspect, the foregoing object is obtained by providing a method of placing at stents in the branches of a bifurcated target anatomy. The method includes placing a first and a second wire guide in a working channel of an endoscope. The first wire guide is inserted into the first branch lumen of the bifurcation. The second wire guide is inserted into the second branch lumen of the bifurcation. A first introducer and splittable catheter can then be advanced over the respective wire guides to the respective target anatomies. Once in place, the first stent can be deployed. A second introducer can then be introduced over the second guide wire, through the splittable catheter and to the proper target anatomy. Once the second introducer is in place, the second stent can be deployed.

The method of the invention may further include any of the following steps: disposing the first introducer and the splittable catheter within the working channel of the endoscope such that the first introducer proximal portion is disposed adjacent to the splittable catheter and the first introducer distal portion is disposed distal to the splittable catheter while inside the working channel of the endoscope; deploying the first stent within the first branch lumen and the main lumen of the bifurcation and withdrawing the first introducer from the bifurcation; and/or splitting the splittable catheter and withdrawing the splittable catheter from the bifurcation.

DETAILED DESCRIPTION OF THE PREFERRED EMBODIMENTS

Figure 2:
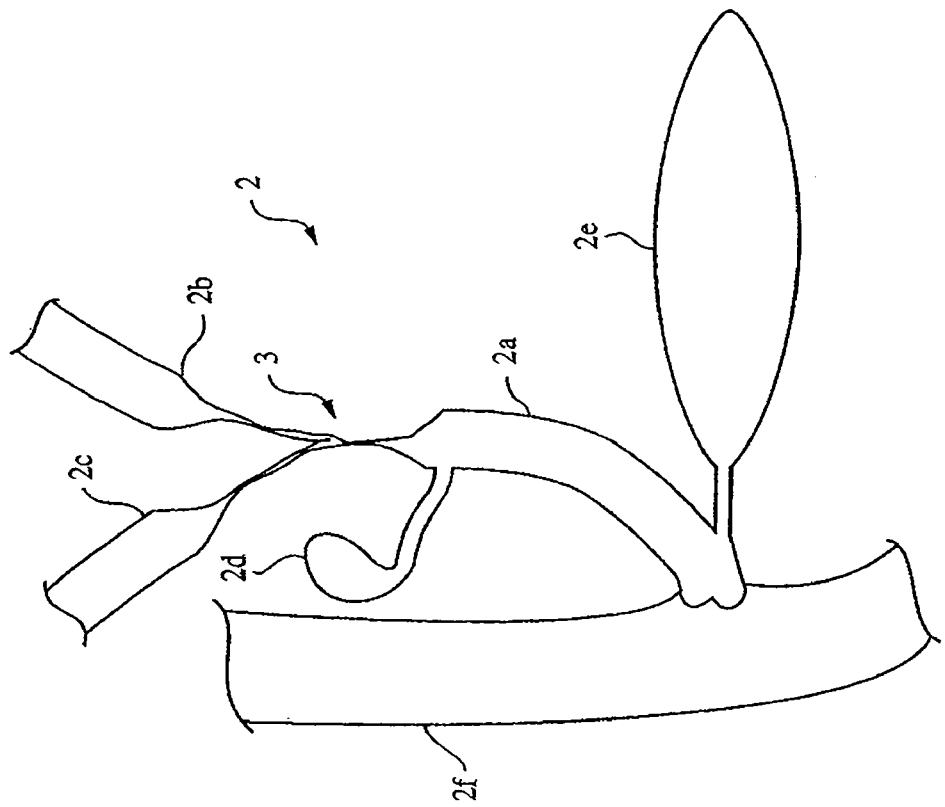
FIG. 2 is a partial, cross-sectional view of the biliary system of FIG. 1 showing strictures within the common bile duct, the left hepatic duct and the right hepatic duct.
Figure 1:
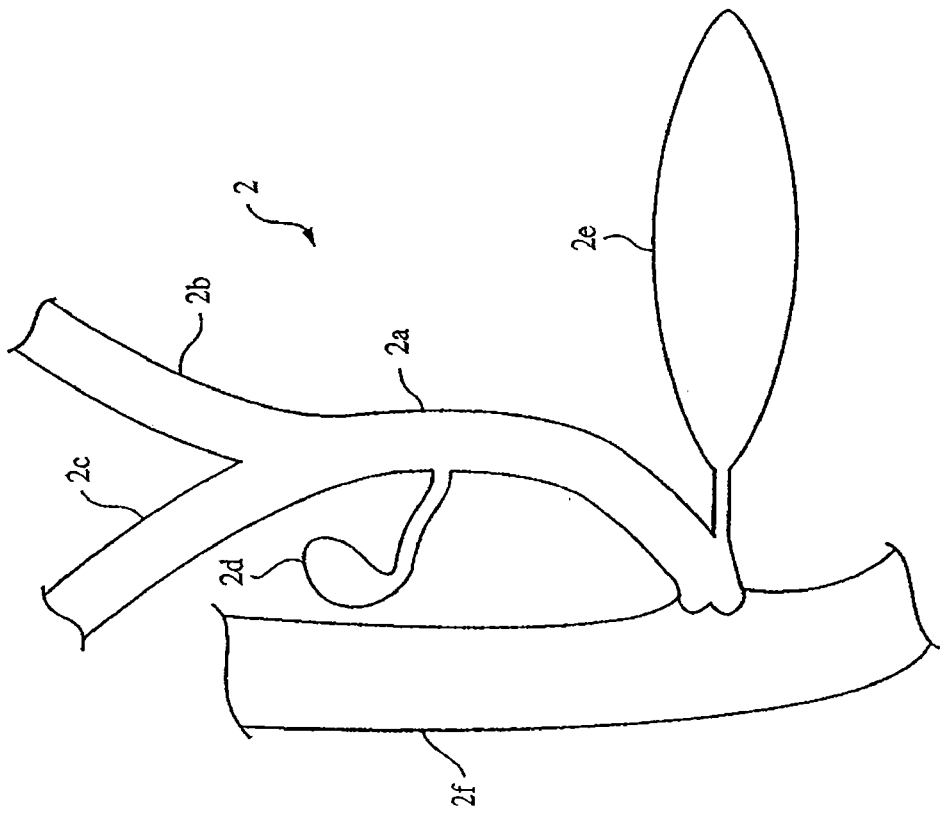
FIG. 1 is a partial, cross-sectional view of a biliary system showing the common bile duct, the left hepatic duct, the right hepatic duct, the gall bladder, the pancreas and the duodenum.
Figure 3A:
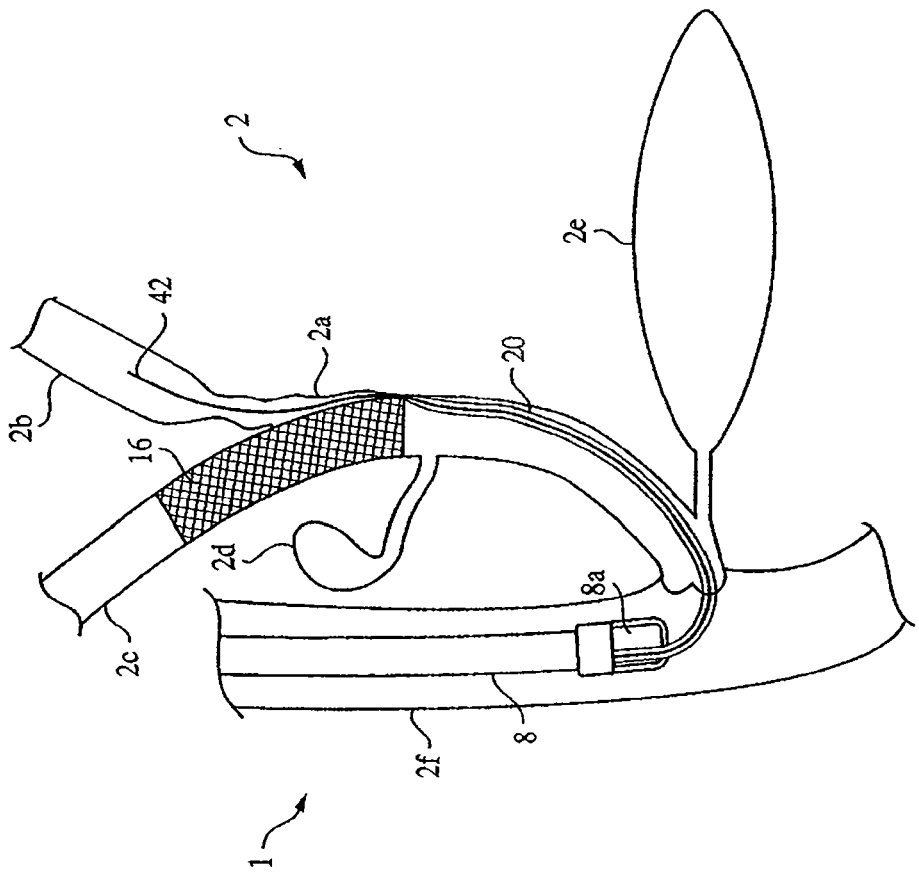
FIG. 3A is a partial, cross-sectional view of the biliary system of FIG. 1 illustrating a first stent previously placed by a first introducer in the right hepatic duct and the common bile duct that obscures the access of a second introducer attempting to place a second stent in the left hepatic duct and common bile duct.
Figure 3:
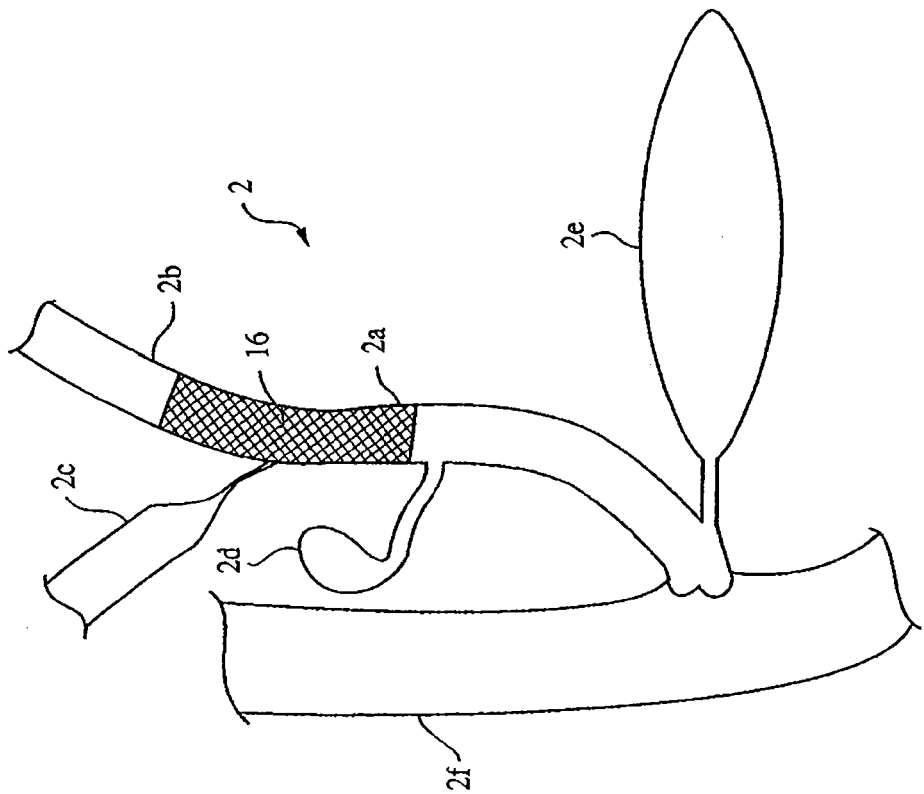
FIG. 3 is a partial, cross-sectional view of the biliary system of FIG. 2 illustrating a stent that has been placed in the common bile duct and the left hepatic duct.
Figure 4:
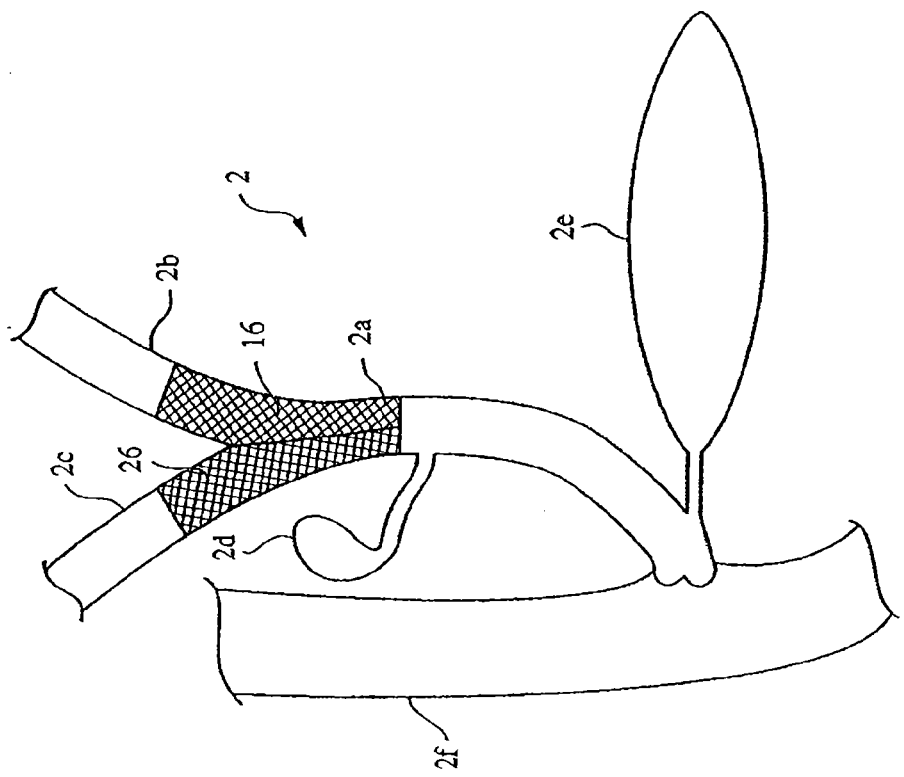
FIG. 4 is a partial, cross-sectional view of the biliary system of FIG. 2 illustrating the placement of first and second stents in the left and right hepatic ducts, respectively, and the common bile duct according to a preferred method of the present invention.

Referring now to the Figures wherein like numerals indicate the same element throughout the views, there is shown in FIGS. 1-2 and 4 a bifurcation having a main lumen, a first branch lumen and a second branch lumen. In particular, these figures illustrate a bifurcation in the biliary system, wherein the main lumen comprises the common bile duct 2a and the first and second branch lumens comprise the left and right hepatic ducts 2b, 2c respectively. FIG. 1 shows a normal, or healthy, biliary system without strictures. FIG. 2 shows the biliary system with strictures 3 residing in the main lumen and in both branch lumens of the bifurcation. FIG. 4 shows a pair of stents placed in the left and right hepatic ducts 2b, 2c, respectively, and the common bile duct 2a according to a method of the present invention.

Figure 5:
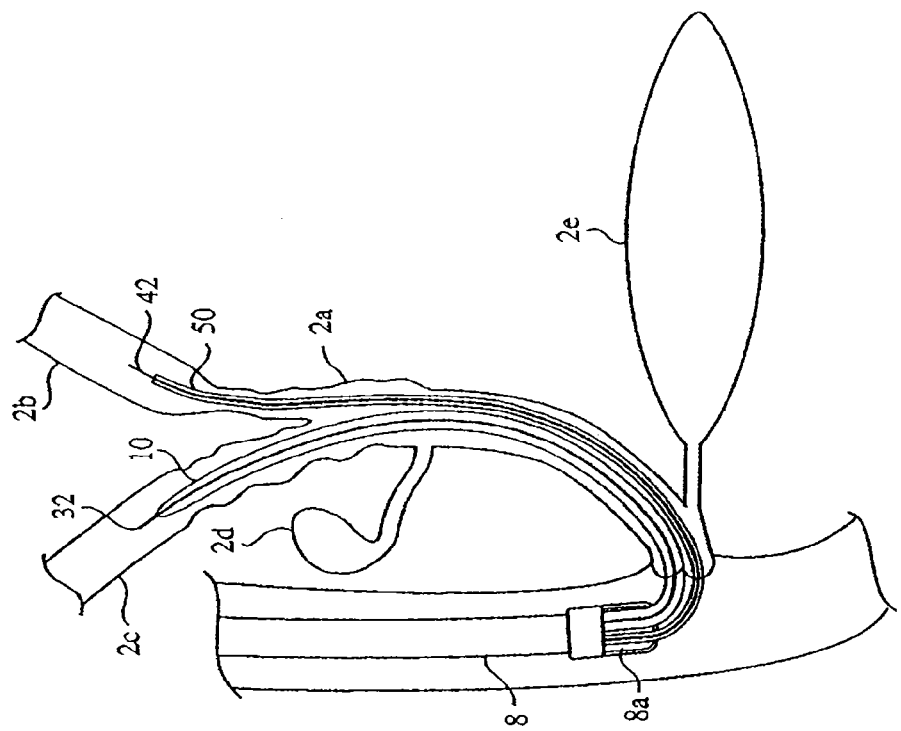
FIG. 5 is a partial, cross-sectional view of a preferred embodiment of the stent delivery system of the present invention illustrating a first introducer placed within the right hepatic duct and the common bile duct and a splittable catheter placed in the right hepatic duct and the common bile duct.
Figure 7:
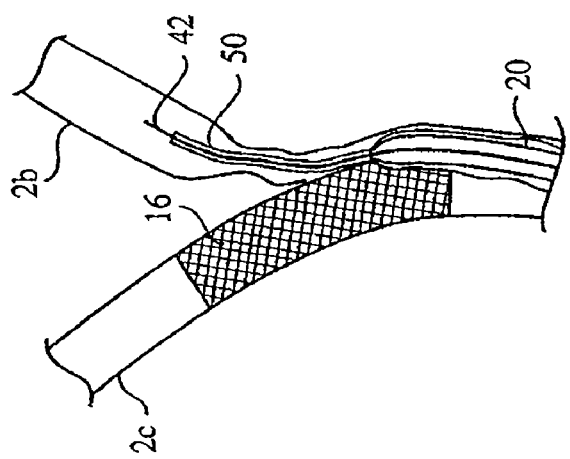
FIG. 7 is a partial, cross-sectional view of the preferred embodiment of the stent delivery system of FIG. 6 illustrating a first stent deployed in the right hepatic duct and common bile duct and the splittable catheter shielding a second introducer as the second introducer is advanced over a second wire guide into the common bile duct and the left hepatic duct.
Figure 8:
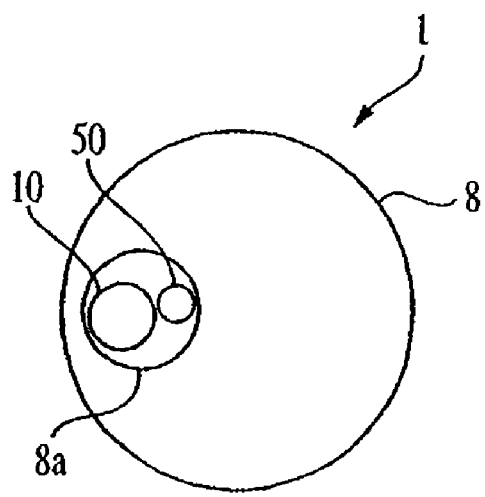
FIG. 8 is a cross-sectional, end view of the stent delivery system of the present invention showing the first introducer and the splittable catheter within the working channel of an endoscope.
Figure 9:
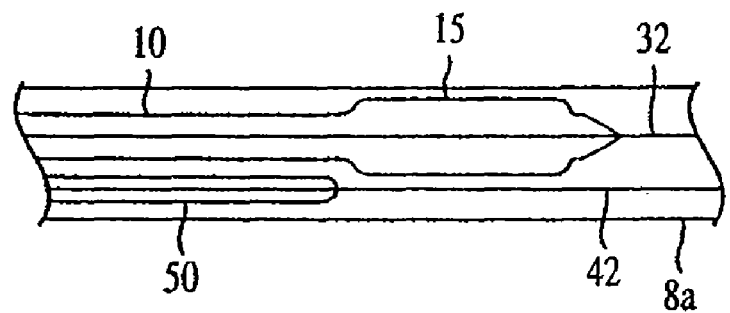
FIG. 9 is a partial, cross sectional, side-view of a preferred embodiment of the stent delivery system of the present invention showing the first introducer and the splittable catheter within the working channel of an endoscope.

Referring now to FIGS. 5-9, a stent delivery system made in accordance with the present disclosure is shown. The stent delivery system includes a first and second introducers configured to deliver two stents to a target anatomy, as well as a catheter used to facilitate delivery of the second introducer to a target anatomy. The first introducer 10 and the splittable catheter 50 are adapted to be disposed within the working channel 8a of an endoscope 8 as shown in FIGS. 5, 8 and 9. As illustrated in FIG. 7, the splittable catheter 50 includes an interior passageway through which the second introducer can be advanced.

As illustrated in FIG. 7, the splittable catheter 50 is an elongate, flexible tube adapted to allow the second introducer 20 to advance unobstructed into the target anatomy. The splittable catheter 50 can be formed from a frangible material, for example, a material that readily tears in a longitudinal direction along the length of the sheath. A non-limiting example of a splittable material is a molecularly oriented (non-isotropic) polytetrafluoroethylene (PTFE) such as that used in the PEEL-AWAY™ Sheath (Cook Incorporated, Bloomington, Ind.). Alternatively, splittable catheter 50 can be formed from any suitable material known in the art including, but not limited to, PTFE, polyamide, polyurethane, polyethylene and nylon including multi-layer or single layer structures. The splittable catheter 50 can also be provided with a groove, pre-score, a weakened area or a pre-slit end to facilitate splitting.

Splittable catheter 50 can ranges in size from about 5 Fr. to about 9 Fr. These sizes are provided for illustrative purposes only and are not intended to be construed as a limitation of the present invention. As one of ordinary skill in the art would appreciate in view of the present disclosure, the size of the splittable catheter 50 is related to the size of the second introducer 20 that is advanced through it, which in turn is related to the size of the second stent 26 in its compressed or unexpanded configuration. Thus, splittable catheters smaller than about 5 Fr. that may become available in the future are contemplated as being within the scope of the claims of the invention.

With respect to the introducers used with the stent delivery system of the present disclosure, any introducer capable of introducing and deploying stents is contemplated. Non-limiting examples include biliary stent deployment delivery systems as well as the introducers described in co-pending provisional application No. 10/728,589, which is incorporated by reference in its entirety. The introducers can be of the same or different type and size.

FIGS. 10-15 illustrate several, non-limiting, exemplary embodiments of introducer 10. In one exemplary embodiment, illustrated in FIG. 10, introducer 10 has a proximal end and a distal end having inner and outer coaxial tubes. The outer coaxial tube forms an outer sheath or catheter 11. The inner coaxial tube forms a shaft 13. Shaft 13 has a proximal end 13a, a distal end 13b and a stent retaining area 15. Optionally, shaft 13 may include a pusher band 17 attached to the stent retaining area 15, a distal tip 18 attached to the shaft distal end 13b and a wire guide lumen 19. Shaft 13 can be made from any suitable material known in the art including, but not limited to, polyethylene ether ketone (PEEK), polytetra-fluoroethylene (PTFE), polyamide, polyurethane, polyethylene and nylon, including multi-layer or single layer structures and may also include reinforcement wires, braid wires, coils and or filaments. Preferably, shaft 13 comprises a proximal portion made of a relatively rigid material such as stainless steel or any other suitable material known in the art.

Stent retaining area 15 is preferably located on a distal portion of the shaft 13. The stent retaining area 15 retains a stent 16 to be deployed in the bifurcation. Optionally, stent 16 is a self-expanding stent.

Pusher band 17 helps to prevent the stent from proximally migrating as the outer catheter 11 is withdrawn proximally to deploy the stent. The pusher band 17 is located proximal to the stent 16 such that the proximal end of the stent 16 abuts the pusher band 17 as shown in FIGS. 10-15.

Figure 12:
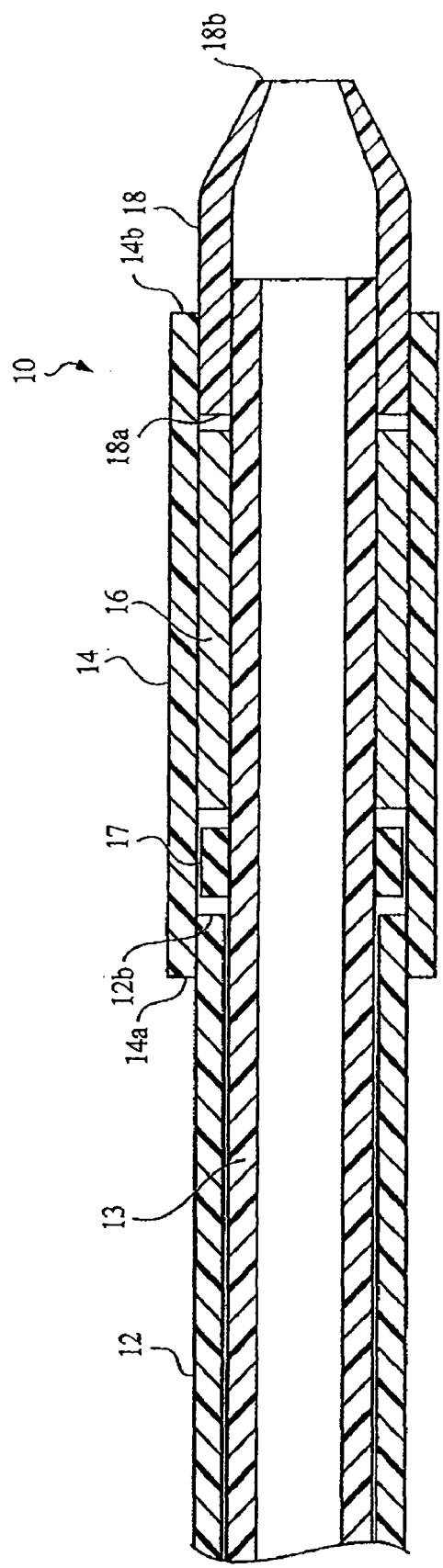
FIG. 12 is a partial, cross-sectional view of an alternate embodiment of the distal portion of the first introducer of FIG. 5.

Distal tip 18 helps prevent fluids from entering the outer catheter 11 as the introducer 10 is navigated through the body lumens. As shown in FIGS. 10-15, distal tip 18 has a proximal end 18a and a distal end 18b. The distal tip proximal end 18a has a diameter that is less than the diameter of the distal outer catheter distal end 14b and is received therein. Optionally, the distal tip 18 tapers to a smaller diameter towards its distal end 18b as shown in FIG. 12. Distal tip 18 can be made from any suitable material known in the art including, but not limited to, PEEK, PTFE, polyamide, polyurethane, polyethylene and nylon, including multi-layer or single layer structures.

Figure 10:
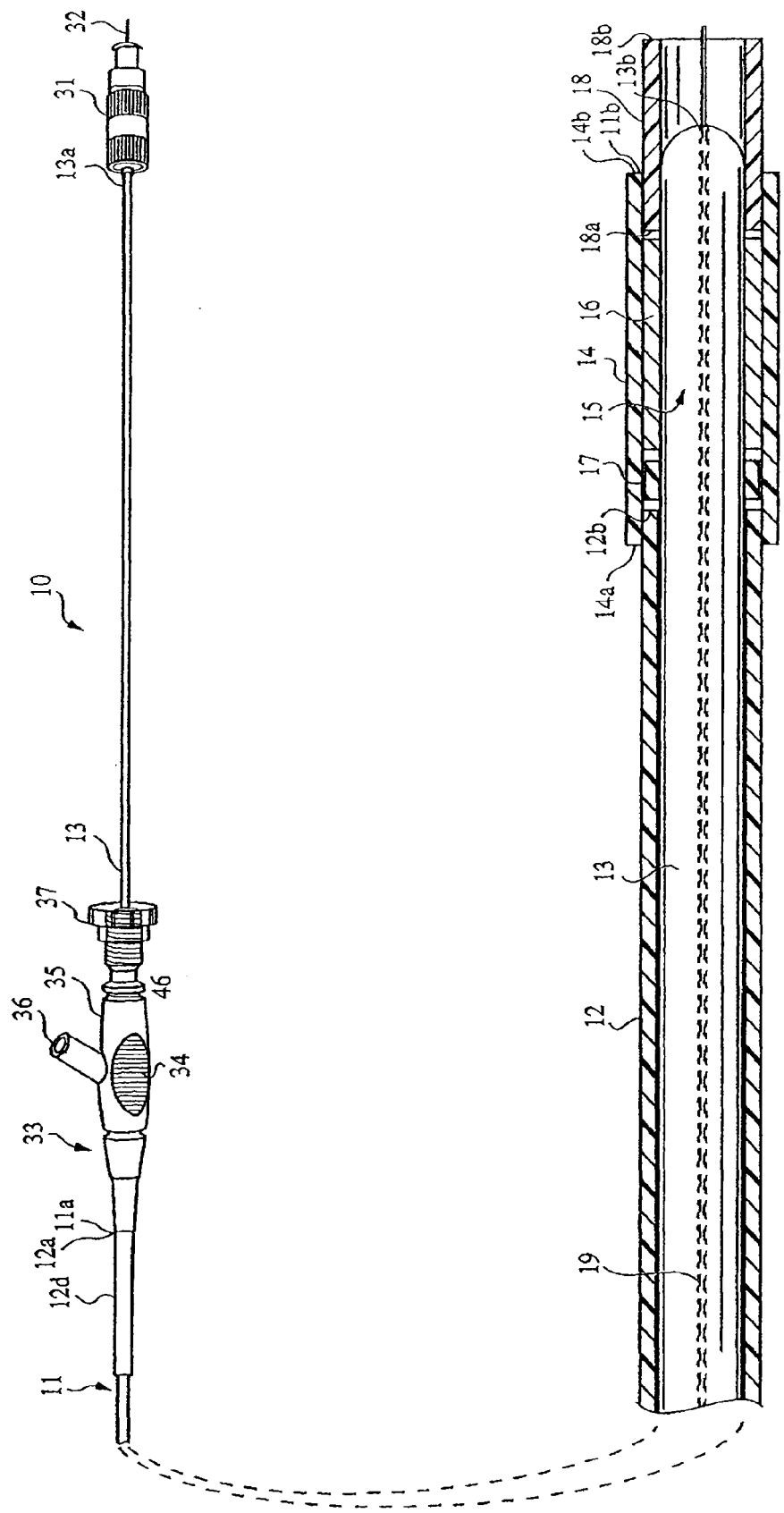
FIG. 10 is a cross-sectional view of an embodiment of the first introducer of the stent delivery system of the present invention.
Figure 11:
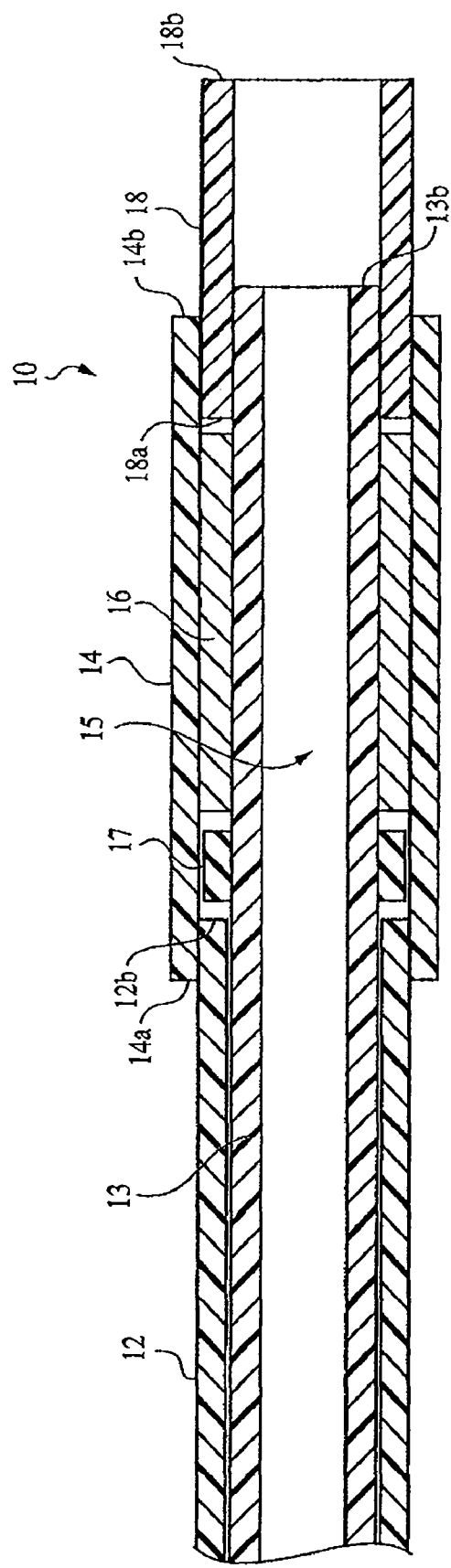
FIG. 11 is a partial, cross-sectional view of a distal portion of the first introducer of FIG. 5.
Figure 13:
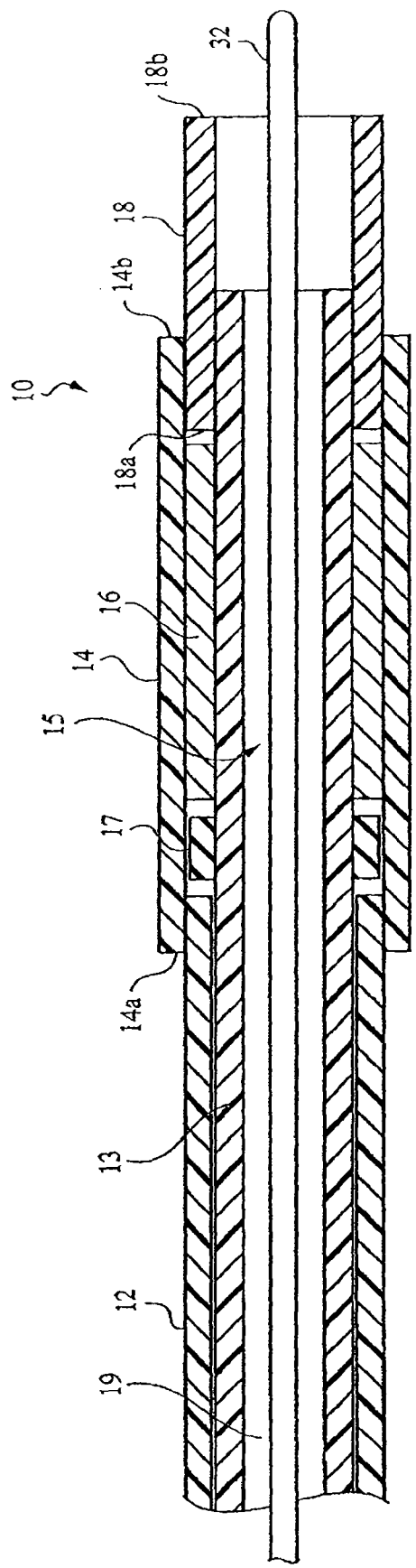
FIG. 13 is a partial, cross-sectional view of the distal portion of the first introducer of FIG. 5 showing the wire guide and wire guide lumen.

In the embodiment shown in FIGS. 10 and 13, wire guide lumen 19 extends through the shaft 13, from the shaft distal end 13b to the shaft proximal end 13a. In this embodiment, the shaft proximal end 13a optionally includes a luer-lock fitting 31 for releasably fixing a wire guide 32 relative to shaft 13 as shown in FIG. 10. In the embodiments shown in FIGS. 10 and 13, the stent delivery system 1 of the present invention includes an over-the-wire type wire guide. Such wire guides are known in the art.

Figure 14:
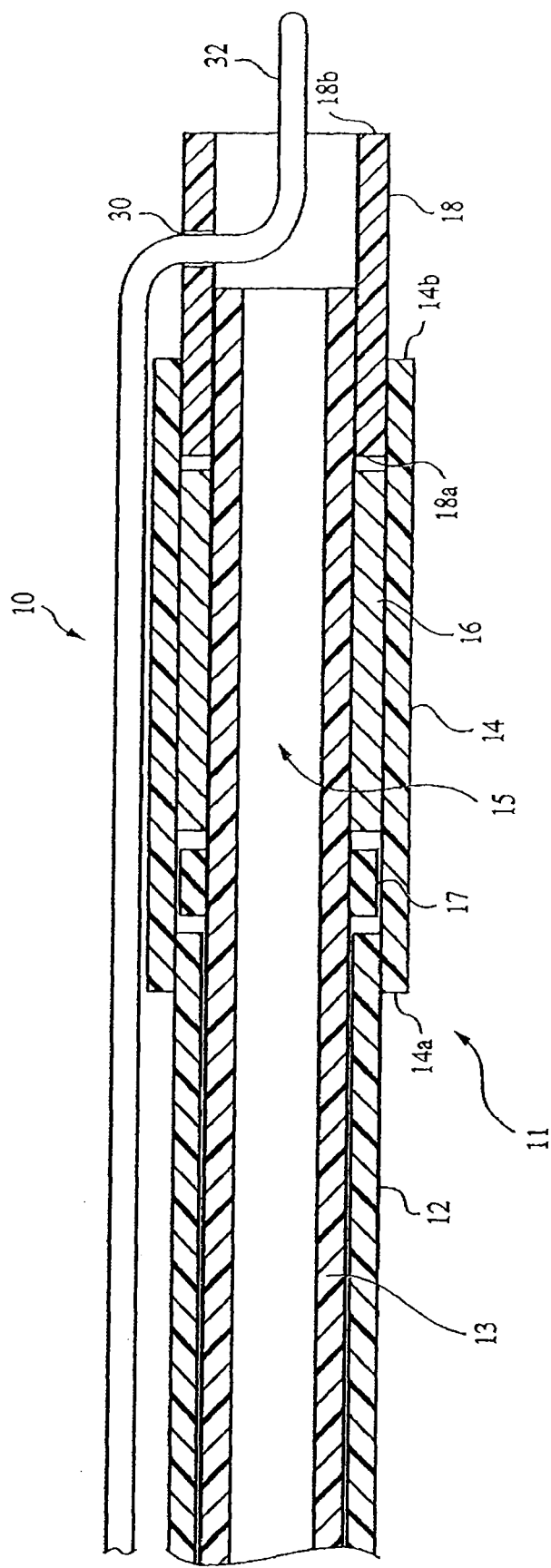
FIG. 14 is a partial, cross-sectional view of the distal portion of the first introducer of FIG. 5 showing an alternate embodiment of the wire guide and the wire guide lumen.

Alternatively, the wire guide lumen 19 may extend through the shaft 13 from the shaft distal end 13b to the shaft proximal end 13a but the wire guide 32 exits through an aperture positioned along the length of the introducer 10. For example, as shown in FIG. 14, the wire guide 32 extends through a portion of the distal tip 18 and exits through an aperture 30 positioned along the length of the distal tip 18. In this embodiment, the wire guide 32 extends through the distal tip 18 and exits the introducer 10 without passing through stent 16. For example, wire guide 32 may extend proximally through distal tip 18 for a distance of about 1 cm.

Figure 15:
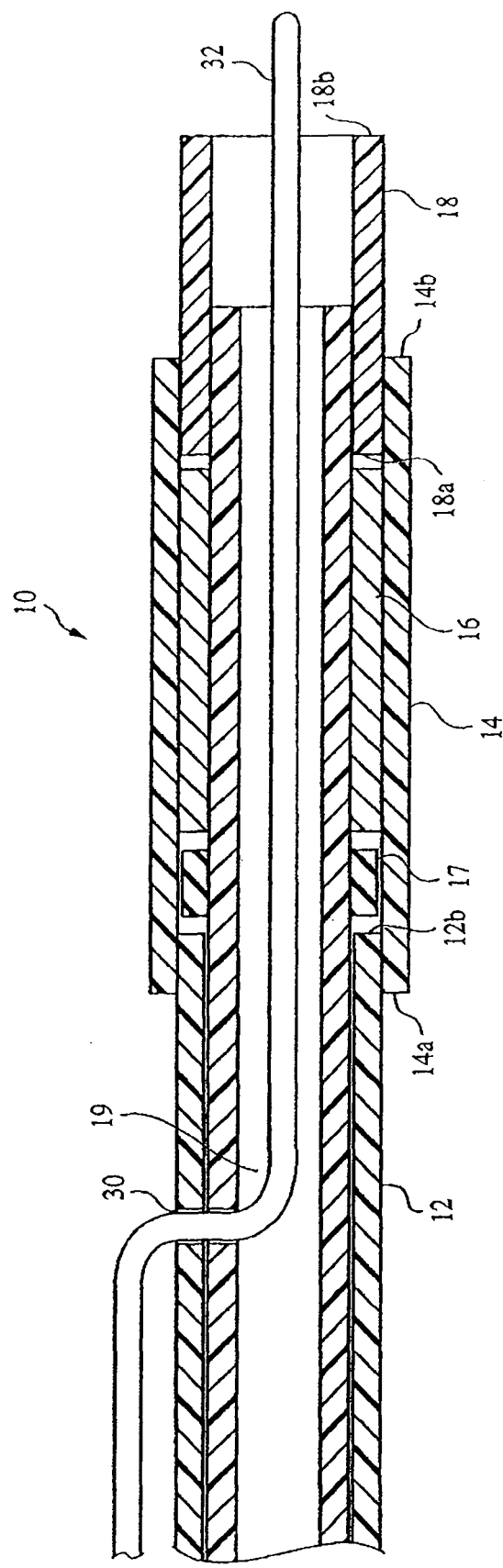
FIG. 15 is a partial, cross-sectional view of the distal portion of the first introducer of FIG. 5 showing an alternate embodiment of the wire guide and the wire guide lumen.

In the alternate embodiment shown in FIG. 15, the wire guide lumen 19 extends through the length of the shaft 13 but the wire guide 32 extends through a portion of the shaft 13 and exits through an aperture 30 positioned along the length of outer catheter 11. In this embodiment, wire guide 32 extends through the distal tip 18, through a portion of the shaft 13 and passes through stent 16 before exiting introducer 10. For example, wire guide 32 may extend through the distal tip 18 and through the stent retaining area 15 for a distance of about 20 cm.

In yet other alternative embodiments, the wire guide lumen 19 may extend through a portion of shaft 13 and may exit through an aperture 30 positioned along the length of the introducer 10. Any number of apertures 30 positioned at any location along the length of the introducer 10 is contemplated. In addition, the wire guide lumen 19 may also comprise a channel or split.

Aperture 30 provides the stent delivery system of the present invention with rapid-exchange capabilities. In particular, by extending the wire guide 32 through only a distal portion of the wire guide lumen 19, the delivery system can be removed from a wire guide 32 having a length substantially shorter than the length necessary if the wire guide 32 were extended through the entire length of the wire guide lumen 19.

Referring to FIG. 10, the sheath or outer catheter 11 has a proximal end 11a and a distal end 11b. Preferably, at least the distal portion of outer catheter 11 is made of any optically clear or imageable material. This allows the stent 16 mounted on the stent retaining area 15 of the shaft 13 to be viewed.

The outer catheter 11 further includes a proximal outer catheter 12 having proximal and distal ends, 12a and 12b, respectively, and a distal outer catheter 14 having proximal and distal ends, 14a and 14b, respectively. The distal end 12b of the proximal outer catheter 12 is attached to the proximal end 14a of the distal outer catheter 14 to form outer catheter 11. The distal end 12b of proximal outer catheter 12 can be attached to the proximal end 14a of distal outer catheter 14 by any method known in the art including, but not limited to, heat fusing, adhesive bonding, chemical bonding or mechanical fitting. Alternatively, the proximal outer catheter 12, and the distal outer catheter 14 can be formed from of a single catheter or sheath.

The introducer proximal outer diameter is between about 5 Fr. and about 6 Fr. The first introducer distal outer diameter is between about 6 Fr. and about 6.5 Fr. This allows placement of a stent having a compressed diameter between about 0.077 inches and about 0.78 inches. These sizes are provided for illustrative purposes only and are not intended to be construed as a limitation of the present invention. As one of ordinary skill in the art would appreciate, the size of the introducer required to place a stent is related to the size of the stent to be placed, and more particularly, to the size of the compressed configuration of the stent. Thus, introducers having distal outer diameters less than about 6 Fr. used to place stents having compressed configurations less than about 0.078 inches that may become available in the future are contemplated as being within the scope of the present disclosure.

The first introducer 10 and the splittable catheter 50 are sized to be disposed next to each other in the working channel 8a of an endoscope 8. More particularly, the sum of the first introducer 10 outer diameter, i.e. either the proximal outer diameter or the distal outer diameter, and the splittable catheter outer diameter is less than the inner diameter of the working channel 8a of the endoscope 8. For example, referring to the embodiment shown in FIG. 9, the first introducer 10 and the splittable catheter 50 are disposed next to each other in a staggered configuration within the working channel 8a of an endoscope 8. That is, the introducer has an increased diameter portion (the stent retaining area) and a decreased diameter portion (the proximal outer catheter). When the introducer and catheter are positioned in an endoscope adjacent to one another and staggered the respective increased and decreased diameter portions are nested together. As can be seen in FIG. 9, the sum of the first introducer proximal outer diameter and the splittable catheter 50 is less than the inner diameter of the working channel 8a of the endoscope 8.

In yet another alternate embodiment of the stent delivery system 1 of the present invention, the first introducer 10 and the splittable catheter 50 are sized to also accommodate at least one wire guide 32 or 42 within the working channel 8a of the endoscope 8. For this embodiment, the sum of the first introducer proximal outer diameter, the splittable catheter outer diameter and at least one of the first and second wire guides 32, 42 is less than the inner diameter of the working channel 8a of the endoscope 8.

Figure 6:
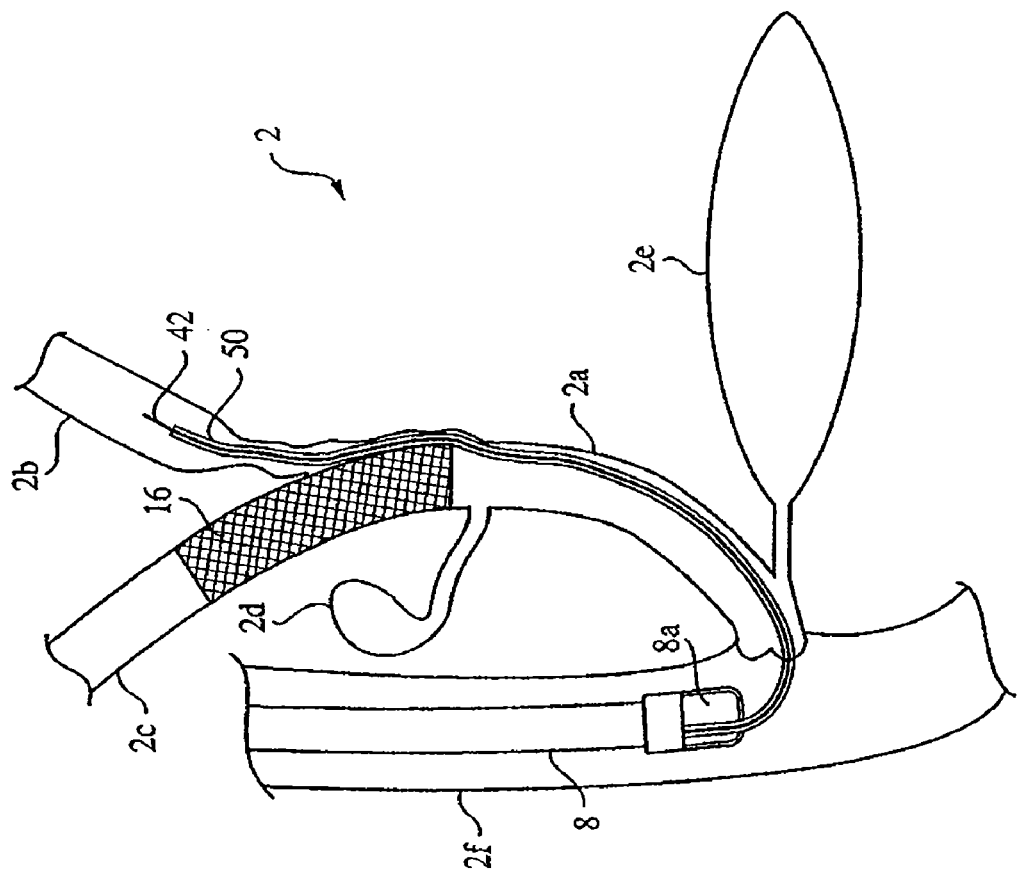
FIG. 6 is a partial, cross-sectional view of the preferred embodiment of the stent delivery system of FIG. 5 illustrating a first stent deployed in the right hepatic duct and common bile duct after the first introducer has been removed and the splittable catheter placed in the right hepatic duct and the common bile duct.

The stent delivery system 1 of the present invention is used to place first and second stents 16, 26 into a bifurcation having strictures 3 in the main lumen 2a and the first and second branch lumens 2b, 2c as follows. Using an endoscope, a distal end of a first wire guide is advanced into the first branch lumen of the bifurcation. A distal end of a second wire guide is then advanced into the second branch lumen of the bifurcation. The first introducer 10 and the splittable catheter 50 are advanced over the wire guide into the working channel 8a of the endoscope 8. Thus, the first introducer 10 is positioned within the first branch of the bifurcation and the splittable catheter 50 is positioned within the second branch lumen of the bifurcation, as shown in FIG. 5. The first introducer 10 and splittable catheter 50 may be positioned sequentially or simultaneously. The first introducer 10 is positioned such that the first stent 16 is at least partially aligned within any occlusion of narrowing of the first branch of the bifurcation. Once aligned, the first stent is deployed within the first branch of the bifurcation and the first introducer is withdrawn as shown in FIG. 6. After the first introducer 10 is removed, a second introducer 20 is passed through the working channel 8a of the endoscope 8 and advanced over the second wire guide 42 through the splittable catheter 50. FIG. 7 shows that the splittable catheter 50 acts as a shield to protect the second introducer 20 from being snagged, or otherwise blocked, by the deployed first stent 16. FIG. 7 also shows the splittable catheter 50 splitting, or peeling away, as the second introducer 20 is advanced through it and into the second branch lumen 26. Once the second introducer 20 is positioned in the second branch lumen 2b, the splittable catheter 50 is removed and the second stent 26 is deployed within the second branch lumen 2b and the main lumen 2a. The resulting connfiguration is shown at FIG. 4.

The above Figures and disclosure are intended to be illustrative and not exhaustive. This description will suggest many variations and alternatives to one of ordinary skill in the art. All such variations and alternatives are intended to be encompassed within the scope of the attached claims. Those familiar with the art may recognize other equivalents to the specific embodiments described herein which equivalents are also intended to be encompassed by the attached claims. For example, the invention has been described in the context of the biliary system for illustrative purposes only. Application of the principles of the invention to any other bifurcated lumens or vessels within the body of a patient, including areas within the digestive tract such as the pancreatic system, as well as areas outside the digestive tract such as other vascular systems, by way of non-limiting examples, are within the ordinary skill in the art and are intended to be encompassed within the scope of the attached claims.

The invention claimed is:

1. A method for propping open a narrowed bifurcated anatomy having a main lumen and first and second branch lumens, the method comprising the steps of:
   a) providing a stent delivery system comprising;
      a first introducer comprising:
         a first tubular body having a first proximal portion, a first distal portion, a first stent carrying portion therebetween, and a first stent;
      a second introducer comprising:
         a second tubular body having a second proximal portion, a second distal portion, a second stent carrying portion therebetween and a second stent;
      a catheter for receiving the second introducer, the catheter having a frangible wall;
      a first wire guide; and
      a second wire guide;
   b) positioning the first introducer and the catheter in a working channel of an endoscope in a staggered configuration;
   c) positioning the endoscope adjacent the bifurcated anatomy;
   d) advancing the first wire guide through the working channel to the first branch lumen;
   e) advancing the second wire guide through the working channel to the second branch lumen, independent of the first introducer ;
   f) advancing the first introducer over the first wire guide to the first branch lumen of the bifurcation;
   g) advancing the catheter over the second wire guide to the second branch lumen of the of the bifurcation; and
   h) deploying the first stent within the first branch lumen and the main lumen;
   i) advancing the second introducer over the wire guide and through the catheter to the second branch lumen wherein advancing the second introducer through the catheter splits the catheter along the frangible wall;
   j) removing the catheter;
   k) deploying the second stent; and
   l) withdrawing the second introducer.

2. The method of claim 1, comprising deploying a portion of the first stent in one of the left hepatic duct and the right hepatic duct and deploying a portion of the second stent in the other of the left hepatic duct and the right hepatic duct.

3. The method of claim 2, comprising deploying a second portion of the first stent and a second portion of the second stent in the common bile duct.

4. The method of claim 1, comprising providing the catheter having an outer diameter that is smaller than an outer diameter of the second introducer.

5. The method of claim 1, comprising removing the first introducer and maintaining the catheter in the second branch lumen of the bifurcation.

6. The method of claim 5, further comprising delivering the second introducer to the second branch lumen through an expandable passageway in the catheter.

7. The method of claim 1, comprising positioning the first proximal portion adjacent to the catheter and the first distal portion distal to the catheter inside the working channel of the endoscope.

8. A method of placing a first stent and a second stent into a bifurcated anatomy using a stent delivery system, the method comprising;
   positioning a first introducer in a working channel of an endoscope, the first introducer comprising a first tubular body having a first proximal portion, a first distal portion, a first stent carrying portion therebetween, and a first stent;
   positioning a catheter adjacent to the first introducer in the working channel of the endoscope, the first distal portion of the first introducer extending distal to a distal end of the catheter within the working channel, the catheter having an expandable passageway;
   advancing the first introducer into a first branch of the bifurcation;
   advancing the catheter into a second branch of the bifurcation independent of the first introducer;
   deploying the first stent in the first branch;
   introducing a second introducer into the expandable passageway of the catheter, the second introducer comprising a second tubular body having a second proximal portion, a second distal portion, a second stent carrying portion therebetween, and a second stent, the second introducer having an outer diameter larger than an outer diameter of the catheter;
   advancing the second introducer over the wire guide and through the catheter to the second branch lumen wherein advancing the second introducer through the catheter splits the catheter along a frangible wall of the catheter;
   removing the catheter;
   deploying the second stent; and
   withdrawing the second introducer.

9. The method of claim 8, comprising deploying the first or the second stent by self expansion.

10. The method of claim 8, comprising positioning a portion of the first introducer in one of the left hepatic duct and the right hepatic duct.

11. The method of claim 10, comprising positioning a portion of the catheter in the other of the left hepatic duct and the right hepatic duct.

12. The method of claim 8, comprising removing the first introducer and maintaining the catheter in the second branch lumen of the bifurcation.

13. The method of claim 8, comprising deploying a first portion of one of the first stent and the second stent in the left hepatic duct and the other of the first portion of the first stent or the second stent in the right hepatic duct.

14. The method of claim 13, comprising deploying a second portion of the first stent and a second portion of the second stent in the common bile duct.

15. A method of placing a first stent and a second stent into a bifurcated anatomy using a stent delivery system, the method comprising:

positioning a first introducer in a working channel of an endoscope, the first introducer comprising a first tubular body having a first proximal portion, a first distal portion, a first stent carrying portion therebetween, and a first stent;

positioning a catheter adjacent to the first introducer in the working channel of the endoscope, the first distal portion of the first introducer extending distal to a distal end of the catheter within the working channel, the catheter having an expandable passageway;

positioning the catheter adjacent the bifurcated anatomy;

advancing the first introducer into a main lumen and a first branch of the bifurcation;

advancing the catheter into the main lumen and a second branch of the bifurcation independent of the first introducer;

deploying the first stent in main lumen and the first branch;

introducing a second introducer into the expandable passageway of the catheter, the second introducer comprising a second tubular body having a second proximal portion, a second distal portion, a second stent carrying portion therebetween, and a second stent, the second introducer having an outer diameter larger than an outer diameter of the catheter;

advancing the second introducer through the catheter thereby splitting the catheter along a frangible wall of the catheter;

withdrawing the catheter; and deploying the second stent in the main lumen and the second branch.

16. The method of claim 15, comprising removing the first introducer before introducing the second introducer into catheter.

* * * * *

UNITED STATES PATENT AND TRADEMARK OFFICE
CERTIFICATE OF CORRECTION

PATENT NO. : 8,029,555 B2  
APPLICATION NO. : 12/689804  
DATED : October 4, 2011  
INVENTOR(S) : Douglas D. Howell et al.

Page 1 of 1

It is certified that error appears in the above-identified patent and that said Letters Patent is hereby corrected as shown below:

<u>On the Title Page</u>

Left column, item (75), after "William S. Gibbons," insert --Jr.,--.

<u>In the Claims</u>

In column 7, claim 1, line 54, after "first" replace "introducer ;" with --introducer;--.

In column 7, claim 1, line 58, before "bifurcation;" replace "of the of the" with --of the--.

Signed and Sealed this  
Twenty-seventh Day of March, 2012

David J. Kappos  
*Director of the United States Patent and Trademark Office*